United States Patent [19]
Naldoni

[11] Patent Number: 5,971,999
[45] Date of Patent: Oct. 26, 1999

[54] APPARATUS FOR MICRODERMABRASION BY MEANS OF A JET OF MIXTURE OF AIR/ REDUCING SUBSTANCES AND RELATING HANDLE

[76] Inventor: Moreno Naldoni, Via Salvador Allende, 22, 50018 Scandicci, Italy

[21] Appl. No.: 08/981,005
[22] PCT Filed: Jun. 14, 1996
[86] PCT No.: PCT/IT96/00122
 § 371 Date: Dec. 16, 1997
 § 102(e) Date: Dec. 16, 1997
[87] PCT Pub. No.: WO97/00050
 PCT Pub. Date: Jan. 3, 1997

[30] Foreign Application Priority Data

Jun. 16, 1995 [IT] Italy .................................. FI95A0135

[51] Int. Cl.$^6$ .................................................... A61B 17/50
[52] U.S. Cl. ............................................ 606/131; 451/87
[58] Field of Search ................................ 606/131; 604/35; 451/87

[56] References Cited

U.S. PATENT DOCUMENTS 5,037,432  8/1991  Molinari .................................. 606/131
5,100,412  3/1992  Rosso ..................................... 606/131

*Primary Examiner*—Michael Buiz
*Assistant Examiner*—Julian W. Woo
*Attorney, Agent, or Firm*—Hazel & Thomas, P.C.

[57] ABSTRACT

This invention is related to an apparatus for microdermoabrasion by means of a jet of a mixture of air and reducing crystals, and the associated handle. The apparatus is used in cosmetic surgery and/or dermatology and utilizes microdermoabrasion wherein a jet of reducing crystals is applied to human tissue. The jet of reducing crystals is, in particular, a jet of corundum crystals ($Al_2O_3$).

6 Claims, 5 Drawing Sheets

APPARATUS FOR MICRODERMABRASION BY MEANS OF A JET OF MIXTURE OF AIR/REDUCING SUBSTANCES AND RELATING HANDLE

TECHNICAL FIELD

This invention is related to an apparatus for microdermabrasion by means of a jet of a mixture of air/reducing substances, and the related handle. The present invention is used in aesthetics and/or dermatology, and concerns in particular an apparatus, and the related handle, for microdermabrasion, so that a jet of reducing substances is applied on human tissue, in particular a jet of corundum crystals ($Al_2O_3$). The present invention can be used for all applications of traditional microdermabrasion, for example:

post acneic scars;

stretch marks;

scars;

hypertrophic scars;

cheloids;

cloasma;

seborrhea;

hyperpigmentation;

fine wrinkles; and cutaneous ageing.

Furthermore, the present apparatus can also be conveniently used in the trichologic field (e.g. peeling of the scalp).

BACKGROUND ART

The known apparatuses for microdermabrasion have three remarkable disadvantages:

(1) internal development of bacterial pockets, which are very difficult to remove;

(2) obstruction of the circuits caused by the mixture of air/reducing substances, wherein said obstruction causes blockage in the apparatus; and (3) possible dispersion in the environment of reducing crystals, together with particles of abraded tissue, which can be infectious.

The European patent application EP-A-0 324 448 (L.I.C.A. of Rosso & C. Snc) and the European patent application EP-A-O 318 042 (Molinari et al.) concern two apparatuses for the micro-abrasion of human epidermis. These devices do not solve either the aforesaid particular hygienic problems or those concerning the obstruction of the circuits. Furthermore, with regard to the handle described in EP-A-0 318 042 (Molinari et al.), it must be specified that it is very expensive for its structure and material. Also apparatuses using monobloc handles made of a glassy material (in particular tempered Pyrex™ have been developed. In this case the handles do not show particular problems concerning obstruction or sterilization, but, because of the particular material they are made of, they are rapidly worn out, thus becoming thinner, so that they could even hurt the patients. All three apparatuses require the pouring out of the crystals, both in the loading and in the unloading phase. Therefore there could be a dispersion of crystals in the environment. If these crystals were used crystals mixed with particles of abraded tissue, there would be a dispersion of potentially infecting material. Furthermore U.S. Pat. No. 3,878,962 (Holbrook et al.) illustrates an improved bottle which can be used for collecting the body fluids of patients in hospital operating rooms. In this bottle the cartridge is closed by means of a quick lock. However, nowhere in U.S. Pat. No. 3,878,962 is it specified that the cartridge filled with unused liquid can be utilized in the following treatment to contain the used liquid.

DISCLOSURE OF INVENTION

The apparatus for microdermabrasion of the present invention was designed according to innovative principles in order to overcome all difficulties which can arise by performing dermabrasion or abrasion of the scalp. The operator using said apparatus is provided with recharging cartridges, each of them containing an amount of corundum which is sufficient for several operations. Once the cartridge is empty, the operator must replace it with a new one by moving the special locking means of the empty cartridge to the full one, and he must perform the opposite procedure with the cartridge containing the used corundum. In this way the cartridge full of dirty crystals, namely mixed with particles of abraded tissue which is potentially infecting, can be sent to the waste disposal without pouring out the crystals, which always causes a certain dispersion of the crystals in the environment, with the concomitant spreading of abraded tissue. With the apparatus of the present invention, the whole loading and unloading of crystals is performed in a few seconds, easily and without spreading the used crystals in the environment. Furthermore, the recharging cartridges can be sterilized, if necessary (previously sterilized cartridge or corundum). The owners of the apparatus can buy the corundum cartridges at the same price as loose corundum. Furthermore, if it were necessary for hygienic reasons, it would be possible to get rid of the recovery cartridges, since they are very cheap (disposable use). The particular handle, which is a further object of the present invention, is composed of three parts which can be completely disassembled without using other tools, thus allowing a quick replacement of the functional block inside it (which is necessary in order to accelerate crystals before the impact with the tissue to be abraded), wherein said replacement allows variation of the "mark" that the crystals jet produce on the epidermis. Said mark can be more or less large and more or less deep according to the length and the section of the small pipe contained in the functional block. The handle is conveniently provided with a plastic grip (e.g. Plexiglass™), whereas the head and the functional block can be made of stainless steel. The inlet and outlet pipes of the crystals are conveniently made of Extraflex™ with a quick joint in suitable pneumatic unions. The object of the present invention is therefore an apparatus for microdermabrasion by means of a jet of a mixture of air and crystals comprising a main body, wherein a vacuum pump and, possibly, a compressor is located, a first mixing container wherein the air is mixed with the crystals, a second recovering container, wherein the used crystals are recovered, and a handle for applying said mixture of air and crystals. The apparatus comprises the first mixing container containing a first locking means including, in its turn, a mixing cannula and a throttle valve, and a first disposable cartridge full of unused crystals. The second recovering container comprises a second locking means including, in its turn, a disposable first filter and a duct, and a second disposable cartridge, said second disposable cartridge being identical to said first disposable cartridge, wherein said first disposable cartridge, once used and emptied, is utilized in the following treatments as said second disposable cartridge.

The problems solved by the present invention can be summarized as follows:

(i) Absolute safety during the loading and unloading of the reducing materials, and possible disposable use of the cartridges;

(ii) No obstruction, since it is possible to reach the crucial points of the circuit, which are the cannula and the functional block containing the small pipe;

(iii) All functional parts are easily accessible and dismountable, thus making easier cleaning and sterilization;

(iv) Choice of cannula and functional block, in order to form the apparatus and the handle which are more suitable for each operation;

(v) No possible contamination of crystals cleaned from abraded human tissue, since the flux of the reducing crystals follows only one direction; and (vi) Possible microdermabrasion operations with a perfect sterility.

BRIEF DESCRIPTION OF DRAWINGS

The present invention will be better understood with reference to the accompanying drawings, which have a purely illustrative and non limiting scope, wherein.

BEST MODE FOR CARRYING OUT THE INVENTION

Figure 1:
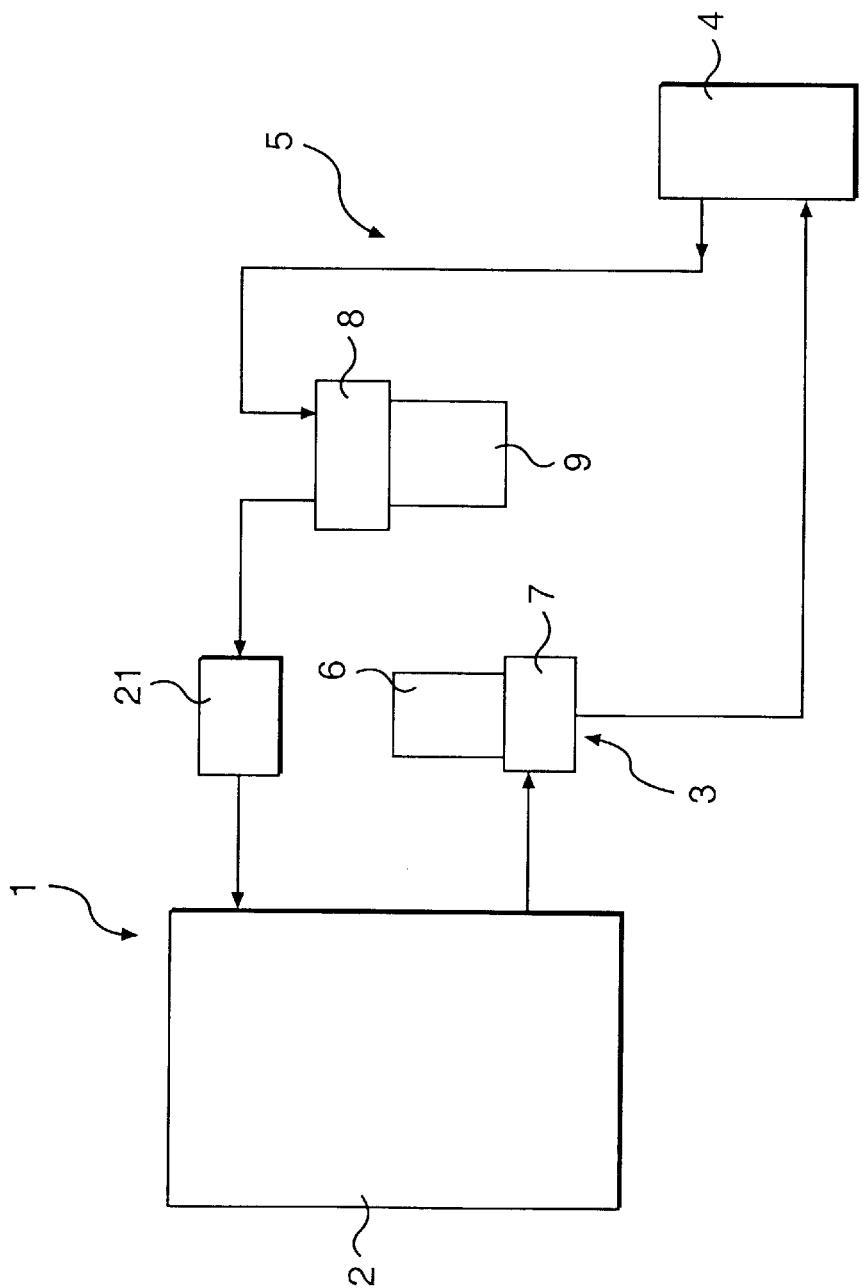
FIG. 1 shows a block diagram of the apparatus of the present invention.

The block diagram of FIG. 1 represents the general structure of the apparatus 1 for microdermabrasion according to the present invention. The main body 2 comprises an inlet pump (not shown in the figure) necessary to the flowing of the mixture of air/reducing substances, an optional compressor necessary to give to the crystals a stronger kinetic energy, wherein said compressor is conveniently run by means of pneumatic controls (pump and pressure switch) and several regulation and display devices. Because of the produced vacuum said pump runs, together with the air sucked in from outside, the corundum crystals present in the mixing container 3, once passed through handle 4, are recovered by the recovery container 5. For a part of the recovery container 5 the applicant conveniently used an empty recharging cartridge 6, which was intended to house the used crystals together with particles of abraded tissue coming from handle 4. Actually, the recharging cartridge 6, once empty, is unscrewed from its locking means 7 and screwed on the other locking means 8. The recovery cartridge 9, full of used crystals and of particles of abraded tissue, can then be expelled during the following cycle.

The operations which must be performed by the operator, both in a conventional apparatus and in the apparatus of the present invention, are the following:

a) turn the apparatus on and start regulation of the required vacuum level;

b) position the handle 4 on the area to be treated;

c) optionally run the compressor by means of the pedal if a deep abrasion is required;

d) pre-set the frequency and duty-cycle if the operator wishes to work with pulsed air.

Figure 2A:
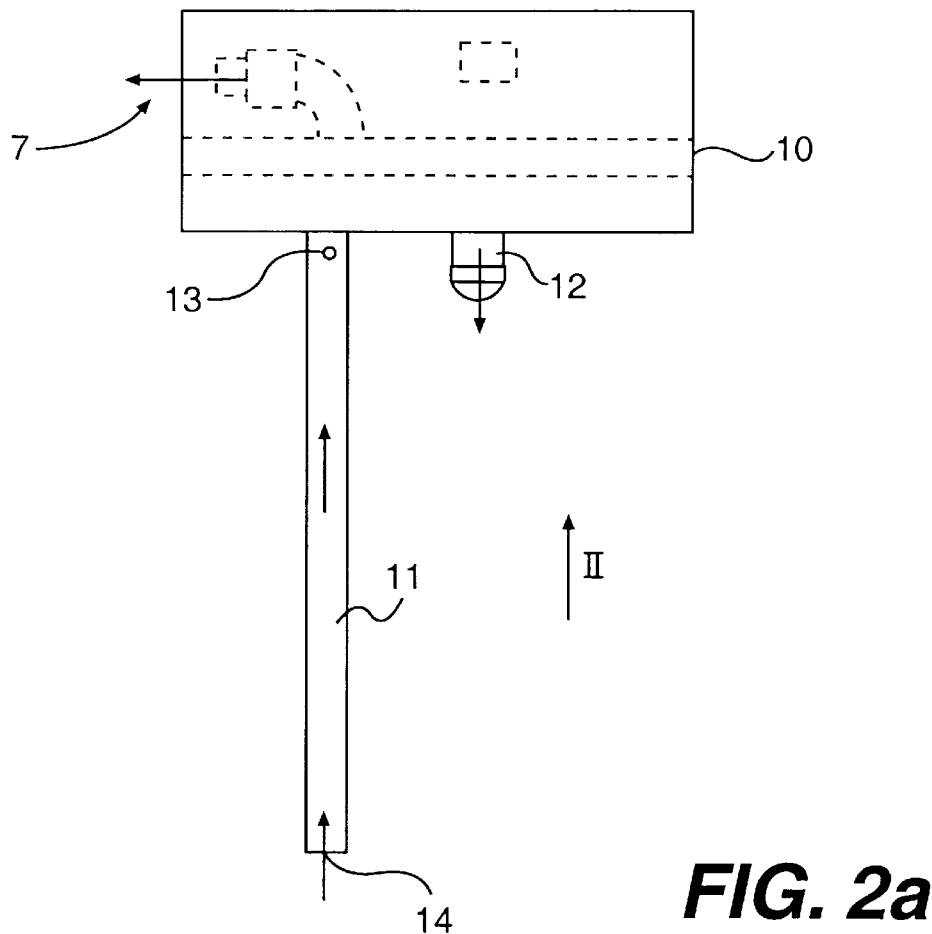
FIGS. 2a and 2b show, respectively, a side view and a view according to arrow II of the locking means of the recharging cartridge.
Figure 2B:
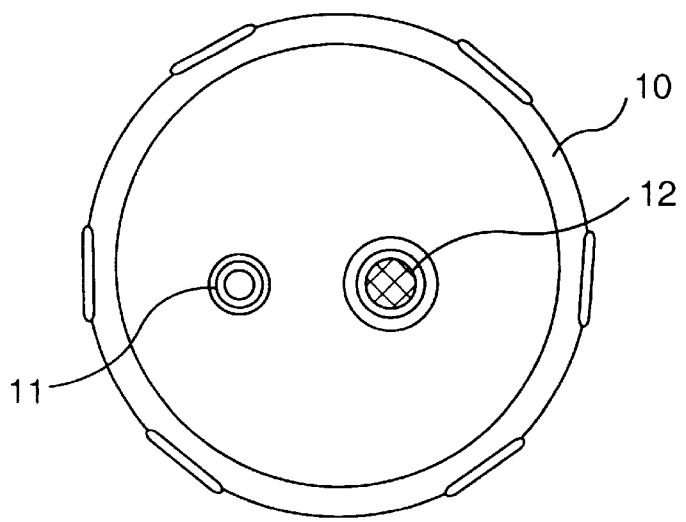
Figure 3A:
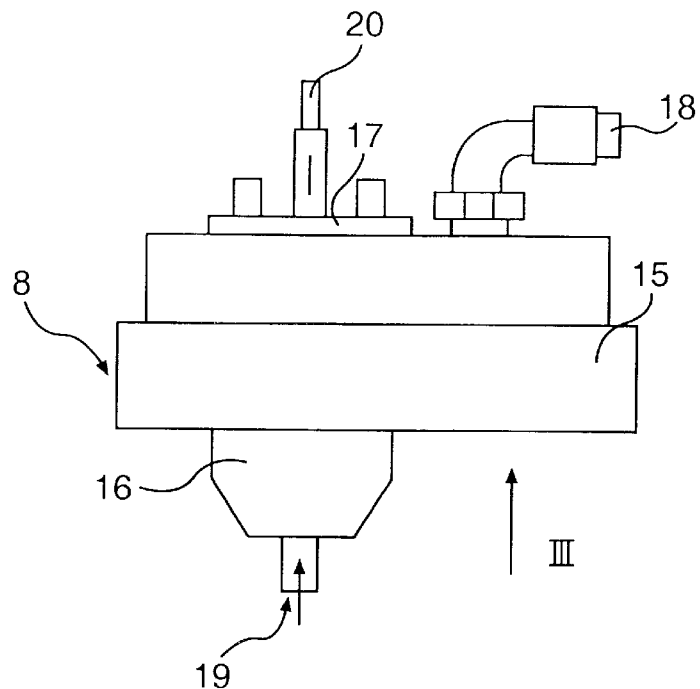
FIGS. 3a and 3b show, respectively, a side view and a view according to arrow III of the locking means of the recovery cartridge.
Figure 3B:
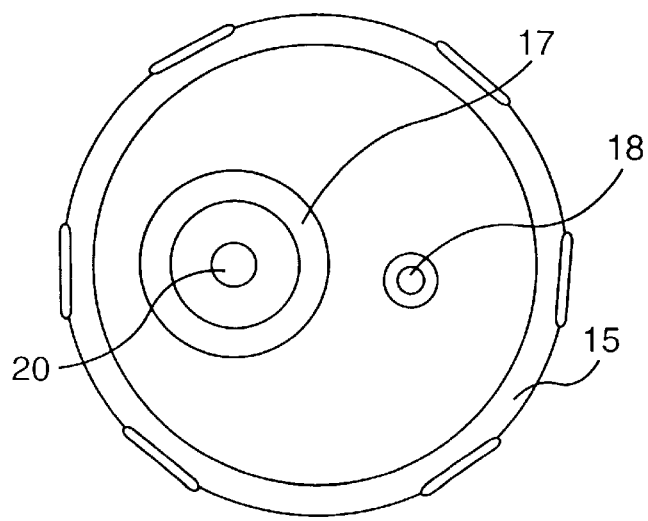

When the operator lays the outlet hole of handle 4 on the skin, the external air mixes with the reducing crystals in the mixing container 3, thanks to the produced depression. This mixture is sent with a strong kinetic energy in the small pipe of handle 4, which accelerates said mixture directing it towards the outlet hole. In the collision, the reducing crystals abrade the skin of the patient and the mixture of air/reducing substances with the removed fragments is sucked in the recovering container 5, wherein both the crystals and the fragments of tissue lie on the bottom. FIGS. 2a and 2b show (upside down) possible locking means 7 for the recharging cartridge 6. It consists of a main body 10, preferably made of aluminum, crossed by a mixing cannula 11 and a throttle valve for the external air 12. The mixing cannula 11 is conveniently made of brass and is simply pressure-fixed, thus allowing an immediate replacement with one of the other cannulas provided with the apparatus. Locking means 7 can also be provided with a pneumatic union for linking it with the outlet duct of the compressor. The lock of locking means 7 on the recharging cartridge 6 is conveniently a quick lock, whereas the vacuum tightness is guaranteed by a suitable o-ring. As already stated, locking means 7 is shown upside down; in fact, in the reality the main body 10 is the base, and the hole 13 of cannula 11 allows the intake of the reducing crystals which are dragged by the air coming in through end 14. It is clear that the easy removal of cannula 11 in order to adapt it to the needs of the user is a relevant element and a further advantage of the present invention. In fact, the choice of the diameter of hole 13 can be made according to the amount of crystals which must be present in the abrading mixture, with the same amount of sucked external air. FIGS. 3a and 3b show locking means 8 of the recovery cartridge 9 forming the recovery container 5. Said locking means 8 consists on its turn of a main body 15 crossed by a first filter 16 (conveniently a disposable one, e.g. a fuel filter) which can be fixed by means of a locknut 17. Locking means 8 is then completed by a duct 18 for the recovery of the used crystals. The aim of the first filter 16, which is cheap and easily replaceable, is to filter the air sucked in by the vacuum pump through the ducts 18, 19 and 20, thus avoiding the passage to the pump of corundum crystals mixed with particles of abraded tissue. Also in this case, it is advantageous to use a quick lock between the locking means 8 and the recovery cartridge 9. In order to improve the safety of the whole apparatus, it is also possible to foresee at the outlet of locking means 8 a second safety filter 21 (FIG. 1), comprising a metal cartridge having a low porosity (5 microns), placed downstream from the first filter 16, which has a further protective aim for the vacuum pump, if there is an accidental boring of said first filter 16. Said second safety filter 21 is externally mounted on the main body 2 and can be inspected and sterilized. Therefore, one of the main principles of the present invention is the use of the cartridges employed for stocking corundum crystals both as recharging cartridges and as recovery cartridges, also foreseeing locking means which can be rapidly coupled with said cartridges. FIGS. 4a, 4b and 5a, 5b show two embodiments of handle 4 for applying the mixture of air/reducing substances on epidermis.

Figure 4A:
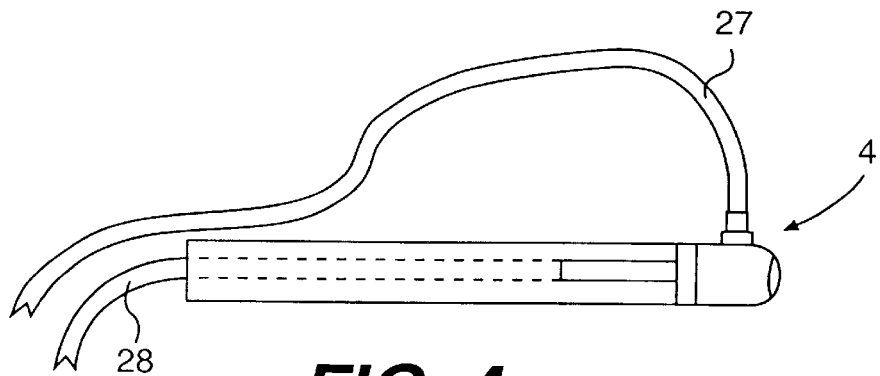
FIGS. 4a and 4b show, respectively, a side view and a longitudinal section of a first embodiment of the handle, which is a further object of the present invention.
Figure 4B:
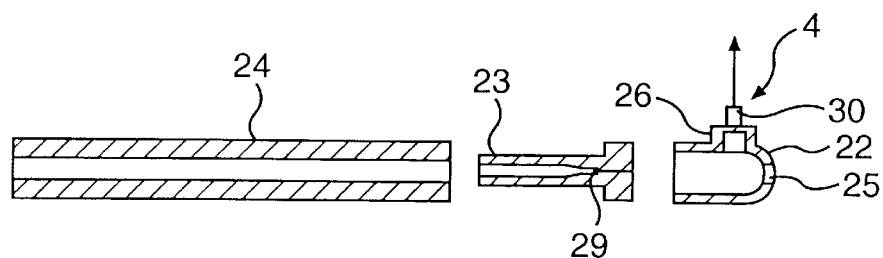

In the first embodiment of FIGS. 4a and 4b, handle 4 is divided into three parts: head 22, functional means 23 and grip 24 (e.g. made of Plexiglass™). Head 22 is provided with an outlet hole 25, through which the reducing mixture is ejected on the skin of the patient, and a lock 26 which is connected to the evacuation pipe 27 of used crystals and particles of removed skin. The mixture of air/reducing substances is sent through the duct 28 (FIG. 4a) to the handle 4. Also the functional block 23 represents a particularly advantageous solution of the present invention. In fact, a rapid replacement of functional block 23 is possible in order to choose the most suitable section and length of the small pipe 29 according to the particular operation that must be performed. In this way it is possible to get on the epidermis of the patient "marks" more or less large and deep in order to have different abrading effects. For example, if you wish to abrade a small spot on the skin without affecting the surrounding tissue, you will choose a functional block 23 provided with a small pipe 29, longer and with a smaller diameter, which is able to send a narrow and powerful sheaf of crystals. If, on the other hand, you wish to treat uniformly a large spot, you will choose a small pipe 29, shorter and with a larger diameter. The head 22 (which can also be made of stainless steel or can be a disposable one made of plastic) can be chosen on its turn with an outlet hole 25 suitable to the used functional block 23. Furthermore, in this first embodiment, the shape of the head 22, having an upper return duct 30 which is perpendicular to the central axis of the head 22, allows the mixture of air/reducing crystals to maintain more kinetic energy at the moment of the impact with the tissue to be abraded. All three elements 22, 23 and 24 forming the handle 4 can be easily assembled and disassembled in order to form the most suitable handle 4 for each operation. The coupling between the head 22 and the functional block 23 can be pressure-fixed or can have a threading, whereas the vacuum sealing effect is guaranteed by a suitable o-ring. According to the aforesaid, the handle 4 is particularly suitable to abrade small regions of the face without affecting the surrounding areas (contour of mouth and eyes), or to remove very small imperfections or spots on the skin, which is a very difficult operation if performed with conventional handles.

Figure 5A:
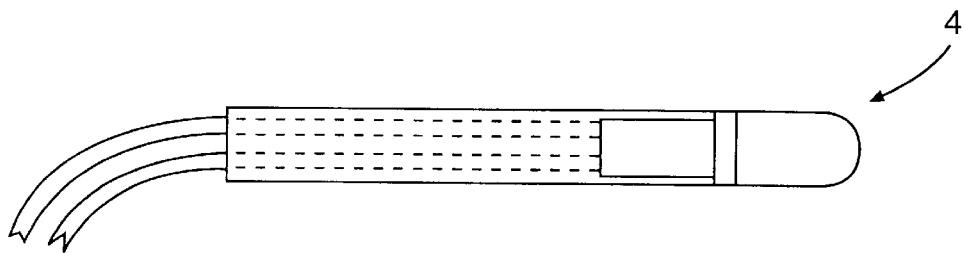
FIGS. 5a and 5b show, respectively, a side view and a longitudinal section of a second embodiment of the handle, which is a further object of the present invention.
Figure 5B:
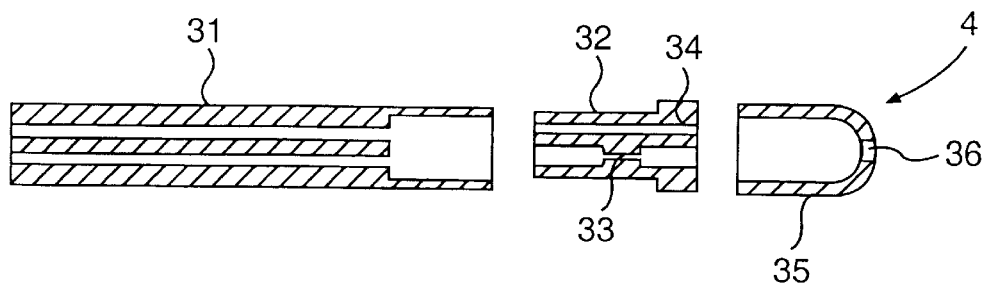

FIGS. 5a and 5b show a second embodiment of the handle 4 which is a further object of the present invention. It consists of a grip 31 (e.g. made of Plexiglass™ or PVC), through which both connecting pipes of handle 4 pass (ejection and recovery), of a functional block 32, which is pressure-fixed inside the grip 31 and comprises both the small pipe 33 and the crystal return duct 34, and of a head 35 presenting an outlet hole 36. The head 35 can be pressure-fixed to the functional block 32 or can be fixed by means of a threading. Said version of the handle 4 offers a very good performance for each kind of use, but is particularly suitable when large areas must be treated. The pulsed working of the apparatus for microdermabrasion object of the present invention is particularly advantageous. This term indicates a device generating pulsed compressed air which sends the air to the handle in order to perform the aforesaid treatments. This new working was created in order to satisfy the necessity of making deep abrasions on small skin areas, reducing to the minimum the warming of the surrounding tissue and the induced pain. Practical tests on patients confirmed the efficiency of said method. Furthermore, it was noticed that, by varying the frequency and the duration of pulses, it is possible to use this method for most applications of microdermabrasion.

Figure 6:
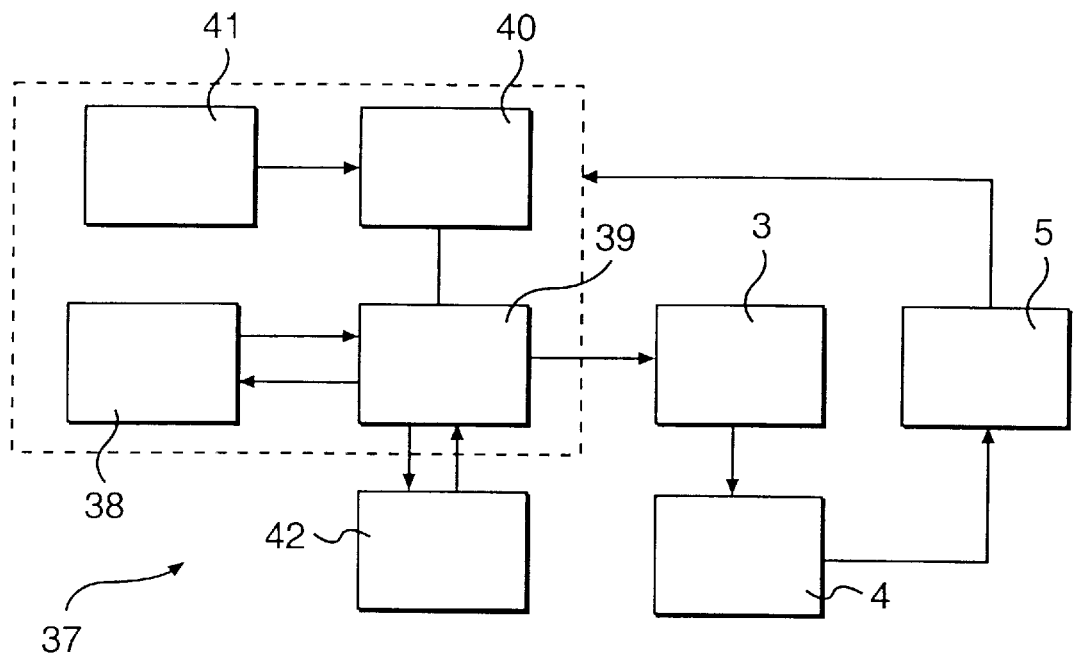
FIG. 6 shows a general plan of the apparatus for microdermabrasion provided with a generator of pulsed compressed air.

FIG. 6 shows the general lay-out of the device generating pulsed and compressed air 37. It comprises a modulator 38, with adjustable frequency and duration, conveniently made by means of a simple electronic circuit, which drives the pneumatic group 39 apt to provide a jet of compressed air with variable pressure (0.5–9 bars). As shown in FIG. 6, said pneumatic group 39 is fed by tank 40, which is filled with air by the compressor 41. Said pulses of compressed air are then suitably sent inside the crystal flowing circuit previously described, thus producing a jet of the mixture of air/crystals coming out from handle 4. This sequence of pneumatic pulses confers to the crystals a remarkable energy, provided within little lapses of time and can produce, as a final effect, deep but scarcely painful abrasions. The pulse timings are conveniently settled in the following way:

frequency: 0.5–50 Hz
duty cycle: 5–50%

The pneumatic group 39 is essentially made of one or more pressure reducers ruling the maximum usable pressure, from a solenoid valve driven by the aforesaid pulse modulator 38 which connects and disconnects the compressed air flux according to pre-set frequency and duration, and of a pressure-switch, driven by the pneumatic pedal 42, acting on the modulator 38. The aforesaid pedal 42 allows a continuous control of air, so that the outlet pressure varies from 0 bars to the maximum pre-set value, according to the strength exerted by the foot on the pedal. Therefore, fully pushing the pneumatic pedal 42, an outlet sequence of pulses is obtained, which have the maximum pre-set pressure, whereas, partially pushing the pedal, pulses provided with an intermediate pressure are obtained. This allows the operator to direct the operation according to his personal feeling, since he can use a continuously modulated regulation by means of the foot pressure on the pneumatic pedal 42.

Figure 7:
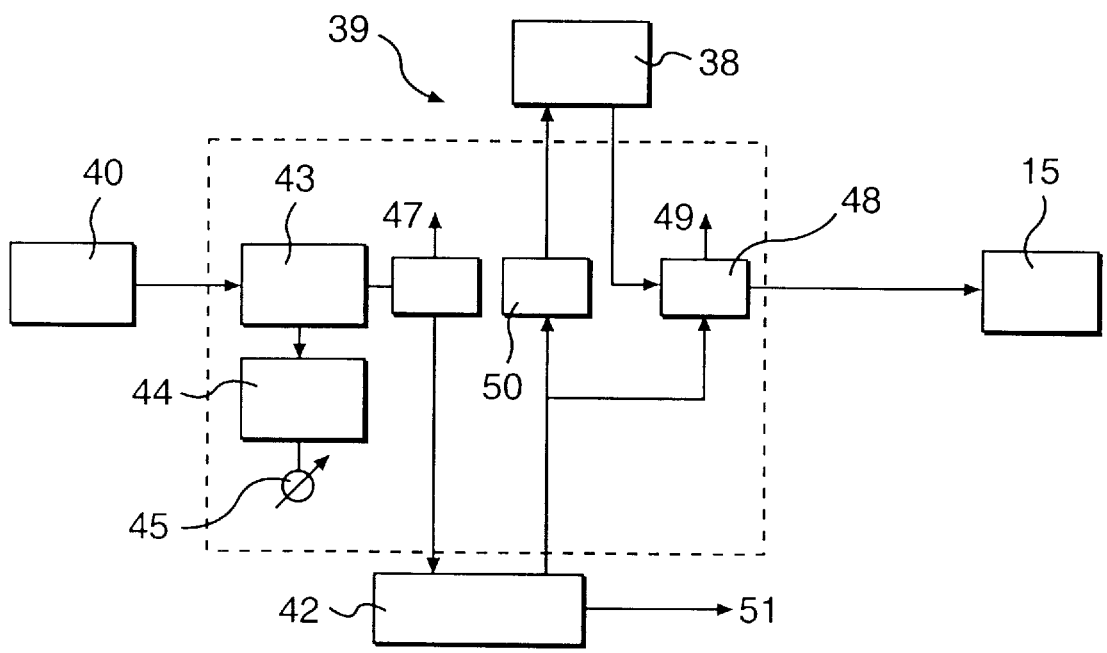
FIG. 7 shows in more detail the pneumatic group belonging to the generator of pulsed compressed air shown in FIG. 6.

FIG. 7 shows in more detail the pneumatic group 39 shown in FIG. 6. The pressure of compressed air going out of the tank 40 is limited by means of a pressure relief device 43, to a maximum value (e.g. 9 bars) which can not be exceeded by the user. Downstream from said pressure relief device 43 there is a pressure regulator 44 driven by the operator, which allows the setting of the maximum pressure (displayed by the pressure gauge 45) required for the treatment. A first solenoid valve controls the taking of the compressed air coming out from the pressure relief device 43, and controls the discharge of the residual pressure through the duct 47, in order to disconnect the pneumatic pedal 42 without producing unsuitable compressed air jets. The pneumatic pedal 42, in its turn, sends the compressed air to a second solenoid valve 48 with a quick discharge, which is also provided with an evacuation duct 49 of the residual air and at the same time it acts on the pressure-switch so, which runs the modulator 38. Said pulse modulator 38 modulates the opening and locking phase of the second solenoid valve 48 with a quick discharge according to the frequency and duration pre-set by the operator. Thus, from the second solenoid valve 48 a series of pulsed compressed air is found, which is directed to the handle 4 through the recharging cartridge 7 containing the clean corundum crystals. The pneumatic pedal 42 is also provided with a discharge duct 51 for the residual air. Said ducts 47, 49, 51 allow evacuation of the residual compressed air present in the various areas of the pneumatic circuit, thus allowing the formation of several pressure pulses.

Without departing from the scope of the present invention, one skilled in the art can make to the apparatus and the handle of the present invention all modifications and improvements suggested by experience and by the natural evolution of technique.

I claim:

1. An apparatus for microdermoabrasion by means of a jet of a mixture of air and crystals comprising:

a main body having a vacuum pump;

a mixing container wherein the air is mixed with the crystals, the mixing container including:
  a first disposable cartridge full of unused crystals; and
  a first locking means having a mixing cannula and a throttle valve;

a recovering container wherein the crystals are recovered after use, the recovering container including:
  a second disposable cartridge which is identical to the first disposable cartridge; and
  a second locking means having a disposable first filter and a duct; and a handle for applying said mixture of air and crystals, wherein said first disposable cartridge, once used and emptied, is utilized as said second disposable cartridge.

2. The apparatus for microdermoabrasion according to claim 1, wherein the main body further comprises a compressor.

3. The apparatus for microdermoabrasion according to claim 1 wherein said mixing cannula is pressure-fixed on the apparatus thus allowing an immediate replacement with an additional mixing cannula provided with the apparatus.

4. The apparatus for microdermoabrasion according to claim 1 wherein said first locking means of said mixing container and said second locking means of said recovering container are quick locks.

5. The apparatus for microdermoabrasion according to claim 1 wherein said first disposable cartridge, full of unused crystals, is easily sterilizable.

6. The apparatus for microdermoabrasion according to claim 1 wherein the crystals are corundum crystals.

* * * * *